United States Patent [19]

Focht

[11] Patent Number: 4,664,805
[45] Date of Patent: May 12, 1987

[54] ANALOG ENRICHMENT DECONTAMINATION PROCESS

[75] Inventor: Dennis D. Focht, Riverside, Calif.

[73] Assignee: Regents of the University of California, Berkeley, Calif.

[21] Appl. No.: 758,190

[22] Filed: Jul. 23, 1985

[51] Int. Cl.$^4$ ............................................... C02F 3/34
[52] U.S. Cl. .................................... 210/611; 210/909; 435/262; 435/823; 435/877
[58] Field of Search ............... 210/601, 610, 611, 908, 210/909; 435/244, 253, 262, 267, 823, 877

[56] References Cited

U.S. PATENT DOCUMENTS 4,169,049  9/1979  Salkinoja-Salonen .......... 210/611 X
4,452,894  6/1984  Olsen et al. ...................... 210/611 X
4,493,895  1/1985  Colaruotolo et al. ............ 20/601 X
4,511,657  4/1985  Colaruotolo et al. ........... 210/611 X
4,514,501  4/1985  Kita et al. ........................ 210/611 X
4,535,061  8/1985  Chakrabarty et al. .......... 210/601 X Primary Examiner—Tom Wyse
Attorney, Agent, or Firm—Nilsson, Robbins, Dalgarn, Berliner, Carson & Wurst

[57] ABSTRACT

Environments contaminated with toxic halogenated organic compounds are decontaminated at an accelerated rate by addition of (1) microorganisms which are non-indigenous to the environment and which metabolize the contaminant at a greater rate than microorganisms indigenous to the environment and (2) a non-toxic analog of the halogenated organic compound.

30 Claims, No Drawings

ANALOG ENRICHMENT DECONTAMINATION PROCESS

BACKGROUND OF THE INVENTION

1. Field of the Invention

This invention relates to a process for the decontamination of environments contaminated with halogenated organic compounds. In one of its more particular aspects, this invention relates to the microbiological degradation of toxic halogenated organic compounds.

Halogenated organic compounds are used in a wide variety of synthetic and utilitarian applications in industry, agriculture, and health care. For example, halogenated organic compounds are used in dielectric fluids, flame retardants, refrigerants, heat transfer fluids, protective coatings, pesticides and other chemical products. Disposal of these materials after use and halogenated by-products of their production poses a serious problem because of the toxicity of many of these halogenated organic compounds. The disposal of toxic waste has, in recent years, achieved such huge proportions that storage of toxic chemicals in landfills and other areas designated for storage thereof no longer satisfies the ever growing need for safe and efficient disposal of these materials.

2. Prior Art

Many different methods have been proposed for rendering toxic wastes innocuous. Among these are incineration, chemical transformation, and microbiological degradation. Because microbiological degradation of toxic waste does not involve the use of chemical reagents which might themselves be toxic and does not result in the production of large amounts of noxious fumes, such as produced in the incineration of toxic waste, it has become a preferred method of disposing of toxic waste.

Most microbiological degradations of toxic materials are based upon discovering a particular microorganism which will metabolize the toxic material, converting it to innocuous metabolic products, usually, in the case of organic compounds, carbon dioxide, water and salts. Finding microorganisms which can efficiently and safely convert toxic wastes into innocuous metabolic products is a highly complex procedure involving many arduous steps and requiring a significant expenditure of time.

One such procedure is taught in U.S. Pat. No. 4,493,895, wherein is described a process for microbial degradation of obnoxious organic wastes into innocuous materials. This process comprises the steps of (1) collecting a sample of material from the site contaminated with obnoxious chemicals; (2) enriching the microorganisms found living in the sample; (3) separating the strains of microorganisms capable of having different metabolisms for the various chemicals in the sample from the site, from each other; (4) purifying the strains which are capable of biodegrading the chemicals to be disposed of; (5) applying the strain to the locus of the contaminants to be disposed of; and (6) monitoring of removal of the contaminants at the locus of the application. It can be seen that this is indeed an involved procedure requiring large amounts of time and effort.

Another approach taught in U.S. Pat. No. 4,511,657 involves a process of treating chemical waste landfill leachates with activated sludge containing bacteria capable of metabolizing obnoxious organics present in the leachates.

In each of these schemes, dependence is placed upon finding a particular microorganism or microorganism-containing sludge to metabolize the obnoxious organic materials constituting the toxic waste. It would be desirable if, rather than simply adding a particular strain of microorganism to the material to be degraded, it were possible to rely upon the microorganisms already present in the environment, that is, microorganisms indigenous to the environment in question, to accomplish the degradation.

Although various aspects of microbiological degradation of organic compounds have been studied, no solution to the problem of utilizing indigenous microorganisms for metabolizing recalcitrant contaminants has been found.

In "Microbial Degradation of Organic Compounds," David T. Gibson, Editor, P. 362, Marcel Dekker, Inc., New York, 1984, the metabolism of commercial PCB mixtures and biphenyl is discussed, but no commercially suitable process is described.

In "Biodegradation of Pesticides," Fumio Matsumura and C. R. Krishna Murti, P. 70, Plenum Press, New York, 1982 the term "cometabolism" is defined to include cases where the microorganisms are induced by chemicals which structurally resemble the pesticide molecules.

I. S. You and R. Bartha describe the increased mineralization of 3,4-dichloroaniline in the presence of aniline in "Stimulation of 3,4-Dichloroaniline Mineralization by Aniline", *Applied And Environmental Microbiology*, 44:678 (1982).

D. D. Focht and M. Alexander describe the cometabolism of various organic compounds structurally related to DDT in "DDT Metabolites and Analogs:Ring Fission by Hydrogenomonas", *Science*, 170:91 (1970).

While these references teach the cometabolism of potentially contaminating organic compounds, no practical process for degrading chlorinated organic compounds in a natural environment is taught.

Cometabolism is reviewed by Raymond S. Horvath in "Microbial Co-Metabolism and the Degradation Of Organic Compounds In Nature", *Bacteriological Reviews*, 36:146 (1972).

R. S. Horvath and P. Flathman in "Co-Metabolism of Fluorobenzoates by Natural Microbial Populations", *Applied And Environmental Microbiology*, 31:889 (1976) describe the oxidation of fluorobenzoic acids by microorganisms which could not utilize these compounds as sole sources of carbon and energy in a basal salts medium and required the addition of glucose to sustain cell growth.

K. Furukawa, N. Tomizuka, and A. Kamibayashi in "Metabolic Breakdown of Kaneclors (Polychlorobiphenyls) and Their Products By Acinetobacter sp.", *Applied And Environmental Microbiology*, 46:140 (1983) describe the utilization of strains of Acinetobacter to metabolize commercial mixtures of polychlorobiphenyls and deduce a pathway for such metabolism.

None of the prior art discloses a commercially useful process for the decontamination of environments contaminated with halogenated organic compounds. None of the references teaches how non-indigenous microorganisms specifically adapted for the metabolism of the contaminant can be utilized with microorganisms indigenous to the environment to accomplish decontamination at a rate which is within practical limits.

It is accordingly an object of the present invention to provide a process for the decontamination of environments contaminated with halogenated organic compounds.

It is another object of the present invention to utilize microorganisms indigenous to such environments in the decontamination thereof.

Another object of this invention is to provide a process whereby the rate of decontamination of such environment can be accelerated.

Other objects and advantages of the present invention will become apparent in the course of the following detailed description.

SUMMARY OF THE INVENTION

The present invention provides a commercially useful process for decontaminating environments contaminated with halogenated organic compounds. The process utilizes microorganisms indigenous to the environment to be decontaminated, an inoculum of microorganisms not indigenous to the environment and a non-toxic analog of the contaminant.

In particular, the present invention provides a process for accelerating the rate of decontamination of an environment contaminated with a toxic halogen containing organic contaminant by microorganisms indigenous to the environment. Such microorganisms cannot grow upon the contaminant. The process includes the steps of adding microorganisms not indigenous to the environment, which cannot grow upon the contaminant and which are capable of metabolizing the contaminant at a rate greater than the rate at which microorganisms indigenous to the environment metabolize the contaminant. Halogen containing metabolic products are produced by the metabolism of the contaminant by the non-indigenous microororganisms enabling the indigenous microorganisms to grow upon such metabolic products. The metabolic products do not, however, support growth of the non-indigenous microorganisms added to the environment. In addition to the non-indigenous microorganisms there is also added to the environment a non-toxic analog of the contaminant, which serves as a substrate for both the indigenous microorganisms and the added non-indigenous microorganisms. In addition, the added analog supports growth of the added non-indigenous microorganisms and the indigenous microorganisms. The result of the addition of the non-indigenous microorganism inoculant and the analog is to build up the population of the indigenous microorganisms which grow upon the analog. The analog also enables the non-indigenous microorganisms added to the environment to grow and to metabolize the contaminant. Growth of the added inoculum and the indigenous microorganisms then continues with the non-indigenous microorganisms metabolizing the contaminant and analog. Meanwhile the indigenous microorganisms continue to metabolize the analog and metabolic products of the contaminant and to grow upon the analog and the metabolic products until the supply of analog is depleted. Thereupon growth of the microorganisms upon the analog ceases and the microorganisms dependent for growth upon the analog die. The indigenous microorganisms continue to grow and to metabolize the metabolic products. Thus, after the non-indigenous microorganisms die, metabolism of the contaminant by the indigenous microorganisms, which can metabolize the metabolic products of the contaminant, continues at an accelerated rate compared to the initial rate at which the indigenous microorganisms metabolize the contaminant.

The advantage of the present invention is that use is made of microorganisms indigenous to the environment to be decontaminated. Acceleration of the rate of decontamination results not only from enhancing the growth of indigenous microorganisms by use of a suitable analog but also by using an inoculum which produces products of metabolism of the contaminant, which can be utilized for growth of the indigenous microorganisms.

DESCRIPTION OF THE PREFERRED EMBODIMENTS

In a preferred embodiment, the present invention makes use of indigenous bacteria, some of which can grow upon halogen-containing metabolic products produced in the microbiological degradation of the contaminant and cannot grow upon the analog added to the environment, others of which can grow upon the added analog but cannot grow upon metabolic products, and still others which can grow upon both substrates. This process is similar to that described above. It consists of the steps of adding to the environment: (a) microorganisms not indigenous to the environment being decontaminated, growth of which is not supported by the contaminant, which non-indigenous microorganisms are capable, however, of metabolizing the contaminant to produce halogen-containing metabolic products at a rate greater than the initial rate at which microorganisms indigenous to the environment metabolize the contaminant. The metabolic products support growth of a first part of the indigenous microorganisms, but do not support growth of a second part of the indigenous microorganisms or growth of the non-indigenous microorganisms. There is also added to the contaminated environment a non-toxic analog of the contaminant, which is metabolized by the second part of the indigenous microorganisms and by the non-indigenous microorganisms. The analog supports growth of the second part of the indigenous microorganisms and the non-indigenous microorganisms, but does not support growth of the first part of the indigenous microorganisms mentioned above. The second step of the process consists in permitting the first part of the indigenous microorganisms to grow upon the metabolic product and the second part of the indigenous microorganisms and the non-indigenous microorganisms to grow upon the analog. The inoculum containing the non-indigenous microorganisms and the analog are added in concentrations such that:

(1) growth of the non-indigenous microorganisms does not inhibit growth of the indigenous microorganisms;

(2) the non-indigenous microorganisms metabolize the contaminant and the analog and grow upon the analog until the supply of analog is depleted to such an extent that growth ceases and they die;

(3) the first part of the indigenous microorganisms grow upon the metabolic products and increase their population;

(4) the second part of the indigenous microorganisms grow upon the analog until the supply of analog is depleted to such an extent that growth ceases and they die; and (5) after the non-indigenous microorganisms and the second part of the indigenous microorganisms die, metabolism by the first part of the indigenous microorganisms proceeds in the absence of the second part of the indigenous microorganisms and the non-indigenous microorganisms at an accelerated rate greater than the initial rate.

Many different environments contaminated with toxic halogenated organic compounds can be decontaminated by means of the process of the present invention. In particular, soils contaminated with such halogen-containing compounds can be rid of the contaminants at a rate which is within practical limits. Aqueous and gaseous environments can also be suitably treated according to the process of the present invention.

A wide variety of toxic halogen containing contaminants find their way into natural environments such as soil, ground water and the atmosphere. Agricultural contaminants which can be degraded according to the process of the present invention include, for example, Heptachlor, Aldrin, Dieldrin, 4,4'-DDE, 4,4'-DDT, Endrin, 4,4'-DDD, Heptachlor Epoxide, Chlordane, Endrin Aldehyde, hexachlorobenzene, and a wide variety of polychlorobiphenyls (PCB's) including Aroclor 1016, 1231, 1232, 1242, 1248, 1254, and 1260. Other chemical contaminants include bis(2-chloroethyl) ether, 1,3-dichlorobenzene, 1,4-dichlorobenzene, 1,2-dichlorobenzene, bis(2-chloroisopropyl) ether, hexachloroethane, bis(2-chloroethoxy)methane, 1,2,4-trichlorobenzene, hexachlorobutadiene, hexachlorocyclopentadiene, 2-chloronaphthalene, 4-chlorophenyl phenyl ether, 4-bromophenyl phenyl ether, 2-chlorophenol, 2,4-dichlorophenol, 4-chloro-3-methylphenol, 2,4,6-trichlorophenol, pentachlorophenol, methylene chloride, trichlorofluoromethane, 1,1-dichloroethylene, 1,1-dichloroethane, 1,2-dichloroethylene, chloroform, 1,2-dichloroethane, 1,1,2-trichloroethane, 1,1,1-trichloroethane, bromodichloromethane 1,2-dichloropropane, trichloroethylene, 1,3-dichloropropane, bromoform, 1,1,2,2-tetrachloroethane, 1,1,2,2-tetrachloroethylene, chlorobenzene, methyl bromide, carbon tetrachloride, 2-chloroethyl vinyl ether, bis(chloroethyl) ether and dichlorodifluoromethane. Other agricultural contaminants including various other pesticides and herbicides and other halogen-containing organics from various sources including industrial wastes can also be similarly treated.

Natural environments contain indigenous microorganisms such as bacteria, fungi, viruses and other microorganisms. Such microorganisms are generally present in mixtures of microorganisms having differing capabilities for metabolizing the undesired contaminants. For example, a given sample of soil may contain microorganisms, some of which are capable of metabolizing the contaminant at so slow a rate that the contaminant persists over an extended period of time without any marked decrease in concentration. Other microorganisms may metabolize the contaminant at a more appreciable rate, but yet not at a rate which is effective to decontaminate the environment within a reasonable period of time. Other indigenous microorganisms may be capable of metabolizing and growing upon analogs of the contaminant.

As pointed out above, there is added to the environment an inoculum of microorganisms which are not indigenous to the environment. These microorganisms are characterized by being capable of metabolizing the contaminant to produce halogen-containing metabolic products at a rate greater than the rate at which the indigenous microorganisms metabolize the contaminant. These non-indigenous microorganisms, though capable of metabolizing the contaminant, cannot grow upon the contaminant. That is, growth of the non-indigenous microorganisms upon the contaminant as the sole source of carbon for growth is impossible. Furthermore, these non-indigenous microorganisms will not grow upon the halogen-containing metabolic products of metabolism of the contaminants, while the indigenous microorganisms or at least a part thereof can grow upon these metabolic products.

Representative of the non-indigenous microorganisms which can be used in the process of the present invention, are three strains which have been deposited with IN VITRO, INTERNATIONAL, INC., Ann Arbor, Mich. These strains have the following designations and taxonomic and morphological characteristics:

*Acinetobacter sp.* (Furukawa), Strain P6, Registration No. IVI 10087. The organism is a gram negative coccoid rod that is catalase positive, cytochrome oxidase negative, non-motile, grows only aerobically, and does not produce acid or gas from glucose. The organism grows in a defined mineral salts medium with biphenyl (0.1%) as a sole carbon source. The mineral salts medium consists of the following: $(NH_4)_2SO_4$, 1 g.; $KH_2PO_4$, 0.2 g.; $K_2HPO_4$, 1.6 g.; $MgSO_4.7H_2O$, 0.2 g.; NaCl, 0.1 g., $FeSO_4.7H_2O$, 0.01 g.; $CaCl_2.2H_2O$, 0.02 g.; deionized water, 1 l. (pH 7.5).

*Pseudomonas putida*, Strain UC-R5, Registration No. IVI 10085. The organism is a gram negative rod that is catalase positive, cytochrome oxidase positive, motile by a single polar flagellum, does not reduce nitrate, grows only aerobically, does not produce fluorescent pigment on either King's A or B agar, hydrolyzes arginine, does not hydrolyze gelatin, and produces neither acid nor gas from glucose. The organism grows in a defined mineral salts medium with 3-chlorobenzoate (0.1%) as a sole carbon source, but not with phenol (0.05%). The mineral salts medium consists of the following: $KH_2PO_4$, 1.36 g.; $Na_2HPO_4$, 2.13 g.; $(NH_4)_2SO_4$, 0.5 g.; $M_gSO_4.7H_2O$, 0.2g.; $CaCl_2$, 5.3 mg.; $FeSO_4.7H_2O$, 2.0 mg.; $MnSO_4.5H_2O$, 0.2 mg.; $CuSO_4.5H_2O$, 0.4 mg.; $ZnSO_4.7H_2O$, 0.2 mg.; $H_3BO_3$, 0.03 mg.; $CoCl_2$, 0.04 mg.; $Na_2MoO_4.2H_2O$, 0.04 mg.; deionized water, 1 l. (pH 6.9).

*Pseudomonas putida*, Strain UC-P2, Registration No. IVI 10086. This strain has the same taxonomic and morphological characteristics as Strain UC-R5 except that it utilizes phenol (0.05%) but not 3-chlorobenzoate (0.1%) as a sole carbon source.

There is also added to the environment a non-toxic analog of the contaminant, which serves as a substrate for the microorganism inoculant and for at least some of the indigenous microorganisms as well. This non-toxic analog can be an organic compound structurally related to the contaminant which, however, generally contains fewer halogen atoms than the contaminant. In some cases, the analog may be a position isomer of the contaminant rather than a less highly halogenated derivative thereof. The analog is metabolized by and supports growth of the non-indigenous microorganisms. In addition, the analog is metabolized by at least a part of the indigenous microorganisms present in the environment. In general, the analog supports growth of those indigenous microorganisms which cannot grow upon the metabolic products resulting from microbiological degradation of the contaminant. However, in some cases, the analog is metabolized and supports growth of microorganisms of the same type which can grow upon these metabolic products. Since a wide variety of organic compounds can be utilized as non-toxic analogs of the contaminant which is to be microbiologically degraded, mention will be made of only a few exemplary cases. For polyhalogenated biphenyls (PCB's), a suitable analog might be a less highly halogenated biphenyl or biphenyl itself. In general, compounds having a structure similar to that of the contaminant and which contain no halogen atoms can be used for this purpose. However, it may be desirable in some circumstances to utilize materials which contain some halogen atoms. If the contaminant is a halobenzoate, such as 4-chlorobenzoic acid, 3,4-dichlorobenzoic acid or 3,5-dichlorobenzoic acid, for example, a suitable analog is benzoic acid 3-methylbenzoic acid or 3-chlorobenzoic acid. Where the contaminant is a halogenated phenol, such as 2-chlorophenol, 3-chlorophenol, 4-chlorophenol, 2,3-dichlorophenol, 2,4-dichlorophenol, 2,5-dichlorophenol, 3,4-dichlorophenol or 3,5-dichlorophenol, a suitable analog is phenol.

The non-indigenous microorganisms and analog are added to the environment in concentrations such that growth of the indigenous microorganisms can proceed without being inhibited by growth of the non-indigenous microorganisms. The non-indigenous microorganisms metabolize the contaminant and analog and grow upon the analog until the supply of analog is depleted, whereupon growth ceases and they die. The indigenous microorganisms metabolize and grow upon the metabolic products and the analog. After the non-indigenous microorganisms die, the surviving indigenous microorganisms metabolize the contaminant in the absence of the non-indigenous microorganisms at an accelerated rate greater than the rate at which the indigenous microorganisms originally metabolize the contaminant in the natural environment.

In general, the rate can be accelerated to at least about twenty-five times the initial rate. Higher rates are also possible.

Useful concentrations of inoculum and analog, in the case of soil contaminated with a halogenated organic contaminant, in the range of about $10^{13}$ to $10^{15}$ cells per acre-foot for inoculum and of about 10–1,000 pounds per acre-foot for analog have been found to be effective. Depending upon the makeup of the indigenous microorganisms, the concentration of analog can be varied to insure that the non-indigenous microorganisms metabolize the contaminant to a sufficient extent that the indigenous microorganisms, which can grow upon the metabolic products of the metabolism of the contaminant by the non-indigenous microorganisms, can continue to metabolize the metabolic products after the inoculum dies, so that metabolism of the contaminant thereafter proceeds at an acceptable accelerated rate.

The invention will be better understood by reference to the following examples, which are included for purposes of illustration only and are not intended to limit the scope of the present invention, which is defined in the claims appended hereto.

EXAMPLE 1

A 100 gram sample of air dried Altamont soil from southern California containing 16 g/kg organic matter and having a pH of 6.4 was added to 250 ml. Erlenmeyer flasks and the moisture content adjusted to 50% of the water holding capacity. Soil samples were sprayed with $^{14}C$ Aroclor 1242 to give a concentration of 100 mg/kg. Suspensions of cells of Acinetobacter sp (Furukawa), Strain P6, Registration No. IVI 10087, which had been grown in mineral salts medium supplemented with 0.1% biphenyl, were added in concentrations of $10^5$ and $10^9$ cells/ml. Biphenyl in a concentration of 3.66 g/kg soil was added to some of the flasks as analog. Each flask was connected at both ends to a $CO_2$ trap, which contained 25 ml. of a standardized KOH solution. Total $CO_2$ released from the soil was determined by titration of soil samples in 10 ml. of KOH solution with 5 ml. of 0.375 M $BaCl_2$ and standardized 1 M HCl using phenolphthalein indicator. $^{14}CO_2$ was determined by liquid scintillation counting.

Flasks containing no soil did not liberate $^{14}CO_2$ into the outgoing trap. Flasks to which no analog was added were found to have evolved less than 1% of Aroclor 1242 as $^{14}CO_2$ after 30 days whereas flasks to which inoculum and analog had been added evolved 15–20% as $^{14}CO_2$, and those to which only analog had been added evolved 10% as $^{14}CO_2$ in the same period.

This example illustrates the accelerated rate of microbiological degradation of PCB's which can be realized by using the process of the present invention.

EXAMPLE 2

The procedure of Example 1 was followed using *Pseudomonas putida,* Strain UC-R5, Registration No. IVI 10085, as the microorganism inoculant with 4-chlorobenzoic acid as the contaminant and 3-methylbenzoic acid as the analog. Metabolism of 400 mg/l of 4-chlorobenzoic acid grown with 1,000 mg/l of 3-methylbenzoic acid was accomplished within 48 hours.

EXAMPLE 3

The procedure of Example 1 was followed using *Pseudomonas outida,* Strain UC-P2, Registration No. IVI 10086, as the microorganism inoculant, 4-chlorophenol as the contaminant and phenol as the analog. Metabolism of 100 mg/l of 4-chlorophenol grown with 500 mg/l of phenol was accomplished within 48 hours.

The process of the present invention is capable of accelerating the microbiological degradation of halogen-containing organic compounds by means of a microorganism inoculant and an analog. Advantage is taken in this process of the microbiological capabilities of microorganisms indigenous to the environment which is to be decontaminated. Acceleration of the rate of decontamination results in the process achieving practicality for decontamination of many natural environments.

While certain specific embodiments of the invention have been disclosed as typical, the invention is, of course, not limited to these particular forms, but rather is applicable to all such variations as fall within the scope of the claims. For example, other microorganisms and other analogs than those specifically taught herein can be utilized. In addition, the concentrations applied to natural environments may vary widely within the scope of the present invention.

What is claimed is:

1. A process for accelerating the rate of decontamination of an environment contaminated with a toxic halogen containing organic contaminant by microorganisms indigenous to said environment, growth of which is not supported by said contaminant, which comprises:

adding to said environment:

(a) microorganisms not indigenous to said environment, growth of which is not supported by said contaminant, said non-indigenous microorganisms being capable of metabolizing said contaminant to produce halogen containing metabolic products at a rate greater than the initial rate at which said indigenous microorganisms metabolize said contaminant, said metabolic products supporting growth of said indigenous microorganisms but not supporting growth of said non-indigenous microorganisms; and (b) a non-toxic analog of said contaminant which is metabolized by both said indigenous microorganisms and said non-indigenous microorganisms, said analog supporting growth of both said indigenous microorganisms and said non-indigenous microorganisms; and permitting said indigenous microorganisms to grow upon said analog and said metabolic products and said non-indigenous microorganisms to grow upon said analog, to build up their populations;

said non-indigenous microorganisms and analog being added in concentrations such that:

(1) growth of said non-indigenous microorganisms does not inhibit growth of said indigenous microorganisms;

(2) said non-indigenous microorganisms metabolize said contaminant and said analog, grow upon said analog until the supply thereof is depleted to such an extent that growth ceases and they die; and (3) said indigenous microorganisms metabolize and grow upon said metabolic products and said analog so that, after said non-indigenous microorganisms die, metabolism of said contaminant by said indigenous microorganisms proceeds in the absence of said non-indigenous microorganisms at an accelerated rate greater than said initial rate.

2. A process according to claim 1 wherein said environment is soil.

3. A process according to claim 1 wherein said analog is a derivative of said halogenated organic compound containing fewer halogen atoms than said halogenated organic compound.

4. A process according to claim 1 wherein said analog is a derivative of said halogenated organic compound containing no halogen atoms.

5. A process according to claim 1 wherein said contaminant is a polyhalogenated biphenyl.

6. A process according to claim 5 wherein said analog is a halogenated biphenyl having fewer halogen atoms than said polyhalogenated biphenyl.

7. A process according to claim 5 wherein said analog is biphenyl.

8. A process according to claim 1 wherein said contaminant is a compound selected from the group consisting of 4-chlorobenzoic acid, 3,4-dichlorobenzoic acid and 3,5-dichlorobenzoic acid and said analog is a compound selected from the group consisting of benzoic acid, 3-methylbenzoic acid and 3-chlorobenzoic acid.

9. A process according to claim 1 wherein said contaminant is a compound selected from the group consisting of 2-chlorophenol, 3-chlorophenol, 4-chlorophenol, 2,3-dichlorophenol, 2,4-dichlorophenol, 2,5-dichlorophenol, 3,4-dichlorophenol and 3,5-dichlorophenol and said analog is phenol.

10. A process according to claim 1 wherein said accelerated rate is at least about 25 times said initial rate.

11. A process according to claim 1 wherein said non-indigenous microorganisms are a species of bacteria.

12. A process according to claim 11 wherein said species of bacteria is a species of Acinetobacter.

13. A process according to claim 11 wherein said species of bacteria is a species of Pseudomonas.

14. A process according to claim 13 wherein said species of Pseudomonas is a strain of *Pseudomonas putida*.

15. A process according to claim 1 wherein said non-indigenous microorganisms are added to soil contaminated with said toxic contaminant in a concentration of about $10^{13}$–$10^{15}$ cells per acre-foot and said analog is added in a concentration of about 10–1,000 pounds per acre-foot.

16. A process for accelerating the rate of decontamination of an environment contaminated with a toxic halogen containing organic contaminant by microorganisms indigenous to said environment, growth of which is not supported by said contaminant, which comprises:

adding to said environment:

(a) microorganisms not indigenous to said environment, growth of which is not supported by said contaminant, said non-indigenous microorganisms being capable of metabolizing said contaminant to produce halogen containing metabolic products at a rate greater than the initial rate at which said indigenous microorganisms metabolize said contaminant, said metabolic products supporting growth of a first part of said indigenous microorganisms but not supporting growth of a second part of said indigenous microorganisms or said non-indigenous microorganisms; and (b) a non-toxic analog of said contaminant which is metabolized by said second part of said indigenous microorganisms and by said non-indigenous microorganisms but not by said first part of said indigenous microorganisms, said analog supporting growth of said second part of said indigenous microorganisms and said non-indigenous microorganisms but not supporting growth of said first part of said indigenous microorganisms; and permitting said first part of said indigenous microorganisms to grow upon said metabolic products and said second part of said indigenous microorganisms and said non-indigenous microorganisms to grow upon said analog;

said non-indigenous microorganisms and analog being added in concentrations such that:

(1) growth of said non-indigenous microorganisms does not inhibit growth of said indigenous microorganisms;

(2) said non-indigenous microorganisms metabolize said contaminant and said analog, grow upon said analog until the supply thereof is depleted to such an extent that growth ceases and they die;

(3) said first part of said indigenous microorganisms grow upon said metabolic products and increase their population;

(4) said second part of said indigenous microorganisms grow upon said analog until the supply thereof is depleted to such an extent that growth ceases and they die; and (5) after said non-indigenous microorganisms and said second part of said indigenous microorganisms die, metabolism of said contaminant by said first part of said indigenous microorganisms proceeds in the absence of said second part of said indigenous microorganisms and said non-indigenous microorganisms at an accelerated rate greater than said initial rate.

17. A process according to claim 16 wherein said environment is soil.

18. A process according to claim 16 wherein said analog is a derivative of said halogenated organic compound containing fewer halogen atoms than said halogenated organic compound.

19. A process according to claim 16 wherein said analog is a derivative of said halogenated organic compound containing no halogen atoms.

20. A process according to claim 16 wherein said contaminant is a polyhalogenated biphenyl.

21. A process according to claim 20 wherein said analog is a halogenated biphenyl having fewer halogen atoms than said polyhalogenated biphenyl.

22. A process according to claim 20 wherein said analog is biphenyl.

23. A process according to claim 16 wherein said accelerated rate is at least about 25 times said initial rate.

24. A process according to claim 16 wherein said non-indigenous microorganisms are a species of bacteria.

25. A process according to claim 24 wherein said species of bacteria is a species of Acinetobacter.

26. A process according to claim 16 wherein said non-indigenous microorganisms are added to soil contaminated with said toxic contaminant in a concentration of about $10^{13}$–$10^{15}$ cells per acre-foot and said analog is added in a concentration of about 10–1,000 pounds per acre-foot.

27. A process for accelerating the rate of decontamination of an environment contaminated with a toxic halogen containing organic contaminant by microorganisms indigenous to said environment, growth of which is not supported by said contaminant, which comprises:
adding to said environment:
(a) bacteria of the species Acinebacter sp. (Furukawa), Strain P6, Registration No. IVI 10087 not indigenous to said environment, growth of which is not supported by said contaminant, said non-indigenous bacteria being capable of metabolizing said contaminant to produce halogen containing metabolic products at a rate greater than the initial rate at which said indigenous microorganisms metabolize said contaminants, said metabolic products supporting growth of said indigenous microorganisms but not supporting growth of said non-indigenous bacteria; and
(b) a non-toxic analog of said contaminant which is metabolized by both said indigenous microorganisms and said non-indigenous bacteria, said analog supporting growth of both said indigenous microorganisms and said non-indigenous bacteria; and
permitting said indigenous microorganisms to grow upon said analog and said metabolic products and said non-indigenous bacteria to grow upon said analog, to build up their populations;
said non-indigenous bacteria and analog being added in concentrations such that:
(1) growth of said non-indigenous bacteria does not inhibit growth of said indigenous microorganisms;
(2) said non-indigenous bacteria metabolize said contaminant and said analog, grow upon said analog until the supply thereof is depleted to such an extent that growth ceases and they die; and
(3) said indigenous microorganisms metabolize and grow upon said metabolic products and said analog so that, after said non-indigenous bacteria die, metabolism of said contaminant by said indigenous microorganisms proceeds in the absence of said non-indigenous bacteria at an accelerated rate greater than said initial rate.

28. A process for accelerating the rate of decontamination of an environment contaminated with a toxic halogen containing organic contaminant by microorganisms indigenous to said environment, growth of which is not supported by said contaminant, which comprises:
adding to said environment:
(a) bacteria of the species Pseudomonas putida, Strain UC-R5, Registration No. IVI 10085 not indigenous to said environment, growth of which is not supported by said contaminant, said non-indigenous bacteria being capable of metabolizing said contaminant to produce halogen containing metabolic products at a rate greater than the initial rate at which said indigenous microorganisms metabolize said contaminant, said metabolic products supporting growth of said indigenous microorganisms but not supporting growth of said non-indigenous bacteria; and
(b) a non-toxic analog of said contaminant which is metabolized by both said indigenous microorganisms and said non-idigenous bacteria, said analog supporting growth of both said indigenous microorganisms and said non-indigenous bacteria; and
permitting said indigenous microorganisms to grow upon said analog and said metabolic products and said non-indigenous bacteria to grow upon said analog, to build up their populations;
said non-indigenous bacteria and analog being added in concentrations such that:
(1) growth of said non-indigenous bacteria does not inhibit growth of said indigenous microorganisms;
(2) said non-indigenous bacteria metabolize said contaminant and said analog, grow upon said analog until the supply thereof is depleted to such an extent that growth ceases and they die; and
(3) said indigenous microorganisms metabolize and grow upon said metabolic products and said analog so that, after said non-indigenous bacteria die, metabolism of said contaminant by said indigenous microorganism proceeds in the absence of said non-indigenous bacteria at an accelerated rate greater than said initial rate.

29. A process for accelerating the rate of decontamination of an environment contaminated with a toxic halogen containing organic contaminant by microorganisms indigenous to said environment, growth of which is not supported by said contaminant, which comprises:
adding to said environment:
(a) bacteria of the species Pseudomonas putida, Strain UC-P2, Registration No. IVI 10086 not indigenous to said environment, growth of which is not supported by said contaminant, said non-indigenous bacteria being capable of metabolizing said contaminant to produce halogen containing metabolic products at a rate greater than the initial rate at which said indigenous microorganisms metabolize said contaminant, said metabolic products supporting growth of said indigenous microorganisms but not supporting growth of said non-indigenous bacteria; and (b) a non-toxic analog of said contaminant which is metabolized by both said indigenous microorganisms and said non-indigenous bacteria said analog supporting growth of both said indigenous microorganisms and said non-indigenous bacteria; and permitting said indigenous microorganisms to grow upon said analog and said metabolic products and said non-indigenous bacteria to grow upon said analog, to build up thier populations;

said non-indigenous bacteria and analog being added in concentrations such that:

(1) growth of said non-indigenous bacteria does not inhibit growth of said indigenous microorganisms;

(2) said non-indigenous bacteria metabolize said contaminant and said analog, grow upon said analog until the supply thereof is depleted to such an extent that growth ceases and they die; and (3) said indigenous microorganisms metabolize and grow upon said metabolic products and said analog so that, after said non-indigenous bacteria die, metabolism of said contaminant by said indigenous microorganisms proceeds in the absence of said non-indigenous bacteria at an accelerated rate greater than said initial rate.

30. A process for accelerating the rate of decontamination of an environment contaminated with a toxic halogen containing organic contaminant by microorganisms indigenous to said environment, growth of which is not supported by said contaminant, which comprises:

adding to said environment:

(a) bacteria of the species Acinetobacter sp. (Furukawa) Strain P6, Registration No. IVI 10087 not indigenous to said environment, growth of which is not supported by said contaminant, said non-indigenous bacteria being capable of metabolizing said contaminant to produce halogen containing metabolic products at a rate greater than the initial rate at which said indigenous microorganisms metabolize said contaminant, said metabolic products supporting growth of a first part of said indigenous microorganisms but not supporting growth of a second part of said indigenous microorganisms or said non-indigenous bacteria; and (b) a non-toxic analog of said contaminant which is metabolized by said second part of said indigenous microorganisms and by said non-indigenous bacteria but not by said first part of said indigenous microorgansim, said analog supporting growth of said second part of said indigenous microorganisms and said non-indigenous bacteria but not supporting growth of said first part of said indigenous microorganisms; and permitting said first part of said indigenous microorganisms to grow upon said metabolic products and said second part of said indigenous microorganisms and said non-indigenous bacteria to grow upon said analog;

said non-indigenous bacteria and analog being added in concentrations such that:

(1) growth of said non-indigenous bacteria does not inhibit growth of said indigenous microorganisms;

(2) said non-indigenous bacteria metabolize said contaminant and said analog, grow upon said analog until the supply thereof is depleted to such an extent that growth ceases and they die;

(3) said first part of said indigenous microorganisms grow upon said metabolic products and increase their population;

(4) said second part of said indigenous microorganisms grow upon said analog until the supply thereof is depleted to such an extent that growth ceases and they die; and (5) after said non-indigenous bacteria and said second part of said indigenous microorganisms die, metabolimm of said contaminant by said first part of said indigenous microorganisms proceeds in the absence of said second part of said indigenous microorganisms and said non-indigenous bacteria at an accelerated rate greater than said initial rate.

* * * * *

UNITED STATES PATENT AND TRADEMARK OFFICE
CERTIFICATE OF CORRECTION

PATENT NO. : 4,664,805

DATED : MAY 12, 1987

INVENTOR(S) : DENNIS D. FOCHT

It is certified that error appears in the above-identified patent and that said Letters Patent is hereby corrected as shown below:

```
Col. 1, line 7, before FIELD OF THE INVENTION, delete "1"
Col. 1, line 28, before PRIOR ART, delete "2"
Col. 2, line 29, before S, insert "-"
Col. 6, line 45, after Na₂MoO₄., delete space Col. 8, line 38, change "outida" to "putida"
Col. 11, line 42, change "Acinebacter" to "Acinetobacter"
Col. 12, line 20, change contamiiant" to "contaminant"
Col. 12, line 30, change "metaolized" to "metabolized"
Col. 13, line 12, change "thier" to "their"
Col. 14, line 37, change "metabolimm" to "metabolism"
```

Signed and Sealed this

Twenty-second Day of December, 1987

Attest:

DONALD J. QUIGG

*Attesting Officer*  *Commissioner of Patents and Trademarks*

UNITED STATES PATENT AND TRADEMARK OFFICE
CERTIFICATE OF CORRECTION

PATENT NO.   :   4,664,805
DATED        :   May 12, 1987
INVENTOR(S)  :   Dennis D. Focht It is certified that error appears in the above-identified patent and that said Letters Patent is hereby corrected as shown below:

Column 6, line 20, insert --[now ATCC Designation 55255, American Type Culture Collection, Rockville, Maryland]-- after "IVI 10087".

Column 8, line 3, insert --[now ATCC Designation 55255, American Type Culture Collection, Rockville, Maryland]-- after "IVI 10087".

Column 11, line 43, change "Registration No. IVI 10087" to --ATCC Designation 55255--.

Column 13, line 36, change "Registration No. IVI 10087" to --ATCC Designation 55255--.

Signed and Sealed this

Twenty-fourth Day of November, 1992

Attest:

DOUGLAS B. COMER

*Attesting Officer*   *Acting Commissioner of Patents and Trademarks*